United States Patent [19]

Dowd et al.

[11] Patent Number: 4,956,343

[45] Date of Patent: Sep. 11, 1990

[54] CONTROL OF INSECTS BY ROSEOTOXIN B

[75] Inventors: Patrick F. Dowd, Peoria, Ill.; Richard J. Cole, Albany, Ga.

[73] Assignee: The United States of America as represented by the Secretary of Agriculture, Washington, D.C.

[21] Appl. No.: 188,993

[22] Filed: May 2, 1988

[51] Int. Cl.$^5$ ....................... A61K 37/02; C07K 11/02
[52] U.S. Cl. ..................................... 514/11; 530/317; 530/323
[58] Field of Search .................... 530/317, 323; 514/9, 514/11

[56] References Cited

PUBLICATIONS

James P. Springer et al., "Structure and Conformation of Roseotoxin B," J. Am. Chem. Soc. 106: 2388-2392 (1984).

Saburo Tamura et al., "Destruxins and Piericidins," Chapter 11 In Naturally Occurring Insecticides, M. Jacobson and D. G. Crosby (eds.), Marcel Dekker, NY (1971), pp. 499-513.

J. L. Richard et al., "Biological Effects of Toxic Products from Trichothecium roseum Link," Mycopathol. Mycol. Appl. 40: 161-170 (1970).

Windholz et al., The Merck Index, 10th Edition, No. 58, p. 10 (1983).

Engstrom, Chem. Abstr., vol. 89, No. 192757j (1978).

Dowd et al., Chem. Abstr., vol. 110, No. 70857y (1989) (Abstract of J. Antibiot., 41 (12), pp. 1868-1872 (1988)).

Joffe, Fusarium Species-Their Biology and Toxicology, Wiley, pp. 104-108 (1986).

Dowd et al., J. Antibiot., vol. 41, No. 12, pp. 1868-1872 (12/88).

Primary Examiner—Lester L. Lee
Assistant Examiner—Christina Chan
Attorney, Agent, or Firm—M. Howard Silverstein; John D. Fado; Curtis P. Ribando

[57] ABSTRACT

Roseotoxin B, a cyclodepsipeptide which is relatively nontoxic to mammals was found to cause mortality and significant reduction in growth when fed to neonate larvae of the corn earworm and southern armyworm as a component of the diet. Thus, it may be used to control Lepidopteran insect pests.

4 Claims, No Drawings

CONTROL OF INSECTS BY ROSEOTOXIN B

BACKGROUND OF THE INVENTION

Mycotoxins and other fungal metabolites are thought to serve as chemical defense systems for the fungi that produce them and may also be of use in protecting the food source from consumption by other organisms [see: D. T. Wicklow, "Ecological Approaches to the Study of Mycotoxigenic Fungi," In Toxigenic Fungi—Their Toxins and Health Hazards, H. Kuvata et al. (eds.), Elsevier, New York, pp. 78–86 (1984)].

Roseotoxin B was isolated from extracts of a culture of *Trichothecium roseum* found on moldy corn by Richard et al. [Mycopathol. Mycol. Appl. 39: 231 (1969)]. Doses of purified roseotoxin B killed all test mice when injected intraperitoneally at 166 mg/kg; none of the mice died when given doses of 100 mg/kg [Richard et al., Mycopathol. Mycol. Appl. 40: 161 (1970)].

The structure of roseotoxin B was determined by Springer et al. [J. Am. Chem. Soc. 106 (8): 2388 (1984)]. As shown below, roseotoxin is a cyclic polypeptide in a class known as cyclodepsipeptides. It is closely related structurally to the destruxins which were isolated from *Metarrhizium anisopliae*.

Roseotoxin B, $R^1 = -Me$  $R^2 = -CH_2CH=CH_2$
Destruxin A, $R^1 = H$  $R^2 = -CH_2CH=CH_2$
Destruxin B, $R^1 = H$  $R^2 = -CH_2CH\begin{smallmatrix}CH_3\\CH_3\end{smallmatrix}$ Roseotoxin B differs from its closest relative in the destruxin series, destruxin A, in that the proline moiety in destruxin A is replaced by trans-3-methylproline in roseotoxin B.

Destruxins are substantially more toxic to mammals than roseotoxin B. Kodaira [Res. Repts. Fac. Textile Sericult., Shiushu University, No. 29, Ser. E, Agr. Sericult. No. 5: 1 (1961)] reported that intraperitoneal injections of 1.35 mg/kg of destruxin A caused the death of all mice tested. The mammalian toxicity of destruxin A is therefore approximately 100 times greater than that of roseotoxin B. Destruxin B killed all mice injected with 16.9 mg/kg and is about 10 times more toxic than roseotoxin B.

The destruxins have been found to possess insecticidal activity [Kodaira, supra]. In silk worm larvae injection of 0.28 μg/g of destruxin A caused death while 0.34 μg/g was required for destruxin B to produce the same effect; insecticidal activity in the destruxins appears to parallel toxicity to mammals. The destruxins were not effective as contact poisons and could not be tested as stomach poisons because feeding was severely inhibited. This phagodepressant effect was also noted for the larvae of potato lady beetle, *Epilachma sparsa* [Kodaira, supra] and *Caravsius morosus* [Roberts, In Naturally Occurring Insecticides, M. Jackson et al. (eds.), Marcel Dekker, Inc., New York, p. 509 (1971)].

Roberts [Proc. Joint U.S.-Japan Seminar Microbial Control Insect Pest, Fukuoka, 1967, p. 4 (1968)] also reported that the stick insect and a number of species of lepidoptera were susceptible to the destruxins. Mosquito larvae were killed by administration of 0.4 to 0.1 mg/larva in the culture water.

In addition to the destruxins, other classes of fungal mycotoxins such as aflatoxins and trichothecenes have been reported to be toxic to insects [see: V. F. Wright et al., "Mycotoxins and Other Fungal Metabolites as Insecticides," In Microbial and Viral Pesticides, E. Kurstak (ed.), Marcel Dekker, New York, pp. 559–583 (1982); S. Tamura et al., "Destruxins and Piericidins," In Naturally Occurring Insecticides, M. Jacobsen et al. (eds.), Marcel Dekker, New York, pp. 499–539 (1971). The roseotoxins, however, have not been previously reported to have insecticidal activity.

SUMMARY OF THE INVENTION

We have now discovered that the cyclodepsipeptide, roseotoxin B unexpectedly has high insecticidal activity coupled with its relatively low toxicity to mammals and apparent lack of a phagodepressant effect.

In accordance with this discovery, it is an object of the invention to define a previously unrecognized chemical compound as a pest control agent having potential availability from both biological and synthetic sources.

It is also an object of the invention to provide a new and unobvious use for roseotoxin B.

Other objects and advantages of this invention will become readily apparent from the ensuing description.

DETAILED DESCRIPTION OF THE INVENTION

Roseotoxin B was isolated from rice culture extracts of an isolate of *Trichothecium roseum* from moldy corn as described by Richard [Mycopathol. Mycol. Appl. 39: 231 (1969)]. Pure material was isolated as described in Example 2 following the procedure of Engstrom et al. [J. Agric. Food Chem. 23 (2): 244–253 (1975)] and was tested against insect species as described in Example 3.

As a practical matter, it is envisioned that commercial formulations of the subject pesticidal agent would be prepared directly from fungal extracts, or fractions derived from such extracts, thereby obviating the need to isolate the compound in pure form. It is clear from the fractionation scheme, presented in Example 2 for roseotoxin B, that the compound is soluble in chloroform, ethyl ether, and ethyl acetate. Other suitable solvents could be readily determined by the skilled artisan. Of course, for applications demanding a high degree of specificity, that is, a high level of predictability of the intended response by both target and nontarget organisms, it would normally be preferred to prepare the formulations from pure or substantially pure roseotoxin B. For example, it is possible that extraneous substances in the natural fungal material would have an undesirable masking or antagonistic effect in regard to the intended activity, or a toxic effect toward the nontarget species. These same considerations of purity would be applied to the compound produced synthetically.

The potency of roseotoxin B dictates that it be applied in conjunction with a suitable inert carrier or vehicle as known in the art. Of particular interest are those which are agronomically acceptable. Alcohols, ketones, esters, and aqueous surfactant mixtures are illustrative of suitable carriers. Depending on the substrate, target species, mode of application, and type of response desired, the concentration of active ingredient in the final composition may vary considerably, but typically should be at least about 1.0 ppm. Factors such as phytotoxicity toward the treated plant and tolerance of nontarget species can be used by the skilled artisan in determining the maximum level.

Depending on the pest species, concentration of agent, and method of application, the subject compound acts to control pests by one or more mechanisms, including, for instance, death inducement, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or "pesticidally effective amount" is defined to mean those quantities of agent which will result in a significant mortality rate of a test group as compared to an untreated group. The actual effective amount may vary with the species of pest, stage of larval development, the nature of the substrate, the type of vehicle or carrier, the period of treatment, and other related factors.

To be effective, the agent must be applied to the locus of, or the vicinity of, the pest to be controlled. When the agent is intended as a stomach poison, it is applied in conjunction with its carrier to the pest diet. In the case of plants, the composition will typically be applied to the leaf surfaces or else systemically incorporated. Alternatively, when the agent is to be used as contact poison, any method of topical application, such as direct spraying on the pest or on a substrate which is likely to be contracted by the pest, would be appropriate.

The compound encompassed herein is effective in controlling a variety of insects. Without desiring to be limited thereto, pests of particular interest known to be vulnerable to treatment are agronomically important insects, especially those of the order Lepidoptera.

Roseotoxin B differs from the structurally related destruxins in that it is substantially less toxic to mammals and apparently does not inhibit the feeding of insects. The material is therefore effective as a stomach poison.

The following examples are intended only to further illustrate the invention and are not intended to limit the scope of the invention which is defined by the claims.

EXAMPLE 1

Growth of *Trichothecium roseum* Rice Cultures

A 15-day-old Sabouraud's dextrose agar culture of an isolate of *Trichothecium roseum* (MC-156) from corn was used to make a suspension of spores in $10^4$ polysorbate 80 in phosphate buffered saline, 0.15M, pH 7.4. A 1:10 dilution of this suspension was used as the inoculum suspension.

The rice medium was prepared by placing 75 g of rice in 1-L Erlenmeyer flasks containing 30 ml of distilled water. The flasks were cotton stoppered, placed at room temperature for 1 hr to allow for imbibition, and then were autoclaved for 15 min at 15 psi and 120° C.

Five ml of the spore suspension was used as inoculum for each flask containing rice medium. All flasks were incubated for 6 days at 28° C. and concurrently shaken at 300 rpm in an incubator shaker.

EXAMPLE 2

Isolation and Purification of Roseotoxin B

Fungal rice cultures from each of 30 flasks from Example 1 were extracted three times with 300 ml of diethyl ether. The combined extracts totaled 28 g of a thick oil-like material. The diethyl ether extract was dissolved in a minimum volume of chloroform and a 20-fold excess of petroleum ether was added, mixed, and allowed to stand at 5° C. overnight. This mixture was filtered to remove insoluble material and concentrated to dryness. The residue was dissolved in diethyl ether to a concentration of about 500 mg/ml. Fifteen milliliters of this solution was then applied to a 30×1.5 cm column of neutral aluminum oxide (activity III), previously equilibrated in diethyl ether. The column was eluted by collecting: (a) 10 30-ml fractions of diethyl ether; (b) 10 30-ml fractions of ethyl acetate; and (c) 10 30-ml fractions of ethyl alcohol.

Roseotoxin B in ethyl acetate fractions 3–6 from three neutral alumina columns were combined and concentrated to dryness, dissolved in diethyl ether, and applied to the 100×0.9 cm column of silica gel for dry-column chromatography (activity III).

This column was eluted by collecting (a) 10 30-ml fractions of diethyl ether; (b) 10 15-ml fractions of 80% diethyl ether-20% ethyl acetate; (c) 10 15-ml fractions of 50% diethyl ether-50% ethyl acetate; (d) 10 15-ml fractions of ethyl acetate; and (e) 10 15-ml fractions of ethyl alcohol.

Column fractions were monitored on thin-layer chromatography (TLC) plates of silica gel H (0.25 mm) with ethyl acetate as the developing solvent. The various components were visualized by iodine. Chromatographic purity of roseotoxin B was checked on silica gel H plates with three TLC solvent systems: (a) ethyl acetate; (b) chloroform-methanol (97:3, v/v); and (c) 3-pentanone-acetone (50:50, v/v). Roseotoxin B was recrystallized from ether-petroleum ether. The melting point was determined to be 199°–200° C.

EXAMPLE 3

Evaluation of Insecticidal Activity

Insects. Neonate larvae of *Heliothis zea* and *Spodoptera frugiperda* were used for all assays. They were obtained from laboratory colonies reared on pinto bean-based diet at 27°±1° C., 40±10% relative humidity, and a 14:10 light:dark photoperiod.

The diet used to rear the insects was based on a standard pinto bean diet for many species of lepidoptera and contained the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 1 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated. The agar was added to 250 ml of water and brought to a boil. The other ingredients were blended in a Waring blender until uniformly mixed. The hot agar was added, and blending continued until all ingredients were uniformly mixed.

The pinto bean-based diet was prepared and added in 5-ml quantities to test tubes. The test tubes were held at 60° C. until chemicals were incorporated to prevent solidification of the diet. The roseotoxin B was added in 125 μl of acetone to the liquid diet upon removal from the water bath to give a final concentration of 250–2.5 ppm. The chemical was incorporated into the diets by blending vigorously with a vortex mixer for 20 sec. Preliminary observations with colored solutions of both water and acetone indicated uniform incorporation by this method. The diets were dispensed into culture plates, and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate *H. zea* or *S. frugiperda* larvae was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4, and 7 days, and the surviving larvae were weighed after 7 days. Each chemical set was tested on a total of 40 larvae. Rosetoxin B showed significant activity at concentrations as low as 2.5 ppm, the lowest level tested. No inhibition of feeding was observed. Results of the evaluations are shown in Table I below.

It is understood that the foregoing detailed description is given merely by way of illustration and that modification and variations may be made therein without departing from the spirit and scope of the invention.

TABLE I.

Toxicity of Roseotoxin B and Insecticides to the Fall Armyworm and Corn Earworm

| | 25 ppm | | 2.5 ppm | |
|---|---|---|---|---|
| Compound | Mortality (%) | Wt. reductions (%) | Mortality (%) | Wt. reductions (%) |
| Corn earworm | | | | |
| Roseotoxin B | 38.7 | >95 | 2.5 | 87.8 |
| Insecticides | | | | |
| Permethrin | — | — | 17 | 81 |
| Malathion | — | — | 5.5 | 27 |
| Fall armyworm | | | | |
| Roseotoxin B | 100 | — | 2.5 | 73 |
| Insecticides | | | | |
| Permethrin | — | — | 35 | 94 |
| Malathion | — | — | 30 | 45 |

Mortality values are based on two replicates of ca. 20 insects each, while weight reductions are based on survivors of mortality tests. All chemicals were incorporated into insect diets, and fed to neonate larvae for 1 week.

We claim:

1. A method of controlling insects comprising applying to a locus of said insects an insecticidally effective amount of rosetoxin B.

2. The method as described in claim 1 wherein said insects are Lepidoptera species.

3. The method as described in claim 1 wherein said insects are *Spodoptera frugiperda*.

4. The method as described in claim 1 wherein said insects are *Heliothis zea*.

* * * * *